United States Patent [19]

Shumate et al.

[11] Patent Number: 5,449,770
[45] Date of Patent: Sep. 12, 1995

[54] PROCESS FOR MAKING N-ALKYLAMINO POLYOLS

[75] Inventors: Robert E. Shumate, Cincinnati; Cynthia M. Stark, North College Hill; Jeffrey J. Scheibel; Roland G. Severson, Jr., both of Cincinnati, all of Ohio

[73] Assignee: The Procter & Gamble Company, Cincinnati, Ohio

[21] Appl. No.: 820,712

[22] Filed: Jan. 14, 1992

[51] Int. Cl.⁶ .......................... C07H 1/00; C07H 5/04
[52] U.S. Cl. ..................... 536/55.3; 536/18.5
[58] Field of Search ................. 536/55.3, 18.5

[56] References Cited

U.S. PATENT DOCUMENTS

| | | | |
|---|---|---|---|
| 1,985,424 | 12/1934 | Piggott | 260/124 |
| 2,016,962 | 10/1935 | Flint et al. | 260/127 |
| 2,016,963 | 10/1935 | Flint et al. | 260/127 |
| 2,653,932 | 6/1953 | Schwartz | 260/211 |
| 2,662,073 | 12/1953 | Mehltretter et al. | 260/102 |
| 2,703,798 | 3/1955 | Schwartz | 260/211 |
| 2,844,609 | 7/1958 | Tesoro | 260/404 |
| 2,954,347 | 9/1960 | St. John et al. | 252/109 |
| 2,991,296 | 7/1961 | Scherr | 260/404 |
| 2,993,887 | 7/1961 | Zech | 260/211 |
| 3,257,436 | 6/1966 | Lindner | 260/404 |
| 3,637,495 | 1/1972 | Eckert et al. | 252/8.8 |
| 3,704,228 | 11/1972 | Eckert | 252/117 |
| 3,920,586 | 11/1975 | Bonaparte et al. | 252/531 |
| 3,929,678 | 12/1975 | Laughlin et al. | 252/526 |
| 3,985,669 | 10/1976 | Krummel et al. | 252/116 |
| 3,988,255 | 10/1976 | Seiden | 252/107 |
| 4,094,808 | 6/1978 | Stewart et al. | 252/186 |
| 4,129,511 | 12/1978 | Ogoshi et al. | 252/140 |
| 4,223,163 | 9/1980 | Guilloty | 568/618 |
| 4,292,212 | 9/1981 | Melby | 252/547 |
| 4,483,781 | 11/1984 | Hartman | 252/174.12 |
| 4,540,821 | 9/1985 | Larkin et al. | 564/473 |
| 4,565,647 | 1/1986 | Llenado | 252/354 |
| 4,664,839 | 5/1987 | Rieck | 252/175 |
| 4,704,224 | 11/1987 | Saud | 252/132 |
| 4,843,154 | 6/1989 | Klein et al. | 536/4.1 |
| 5,009,814 | 4/1991 | Kelkenberg et al. | 252/548 |

FOREIGN PATENT DOCUMENTS

| | | |
|---|---|---|
| 206283 | 6/1956 | Australia . |
| 0285768 | 2/1988 | European Pat. Off. . |
| 3112904-A | 5/1991 | Japan . |
| 03246265 | 11/1991 | Japan .................. C07C 233/18 |
| 420518 | 11/1934 | United Kingdom . |
| 519381 | 3/1940 | United Kingdom . |
| 771423 | 4/1957 | United Kingdom . |
| 809060 | 2/1959 | United Kingdom . |

OTHER PUBLICATIONS

"N-D-Gluco-N-methylalkanamide Compounds, a New Class of Non-Ionic Detergents for Membrane Biochemistry", Biochem. J., (1982), vol. 207, pp. 363-366, Hildreth.

H. Kelkenberg, "Detergents Based on Sugars", Tenside Surfactants Detergents, 25, (1988), pp. 8-13.

Relative Stabilities of d-Glucose-Amine Derivatives, Mohammad and Olcott, JACS, Apr. 1947, p. 969, vol. 66.

[23] 1-Amino-1-deoxy-D-glucitol, Long and Bollenback, Meth. Carbohyd. Chem., vol. 2, (1963), pp. 79-83.

The Reaction of Glucose with Some Amines, Mitts and Hixon, JACS, vol. 66, (1944), pp. 483-486.

Synthesis of $^{14}C$-Labeled N-Methylglucamine, Heeg et al., Can. J. of Pharmaceutical Sciences, vol. 10, No. 3, (1975), pp. 75-76.

Synthesis of Long Chain N-Alkyllactylamines from Unprotected Lactose—A New Series of Non-Ionic Surfactants, Latge et al., J. Dispersion Science and Technology, 12(3&4), pp. 227-237 (1991).

*Primary Examiner*—Douglas W. Robinson
*Assistant Examiner*—Gary L. Kunz
*Attorney, Agent, or Firm*—M. D. Jones; J. J. Yetter; J. C. Rasser

[57] ABSTRACT

N-alkylamino polyols substantially free from nickel contamination are prepared by reacting N-alkylamines with reducing sugars in the presence of hydrogen and nickel catalysts under defined conditions of temperature and pressure. The polyols are characterized by their low odor and low color characteristics. Thus, high quality N-methyl glucamine, N-methyl fructamines and the like are secured.

7 Claims, No Drawings

PROCESS FOR MAKING N-ALKYLAMINO POLYOLS

FIELD OF THE INVENTION

The present invention relates to the reaction of N-alkylamines with reducing sugars and hydrogen in the presence of a nickel catalyst to prepare N-alkylamino polyols having low nickel content and low color and odor characteristics.

BACKGROUND OF THE INVENTION

The preparation of N-alkylamino polyols from N-alkylamines, sugars and hydrogen under the influence of nickel catalysis is a known process. However, the resulting N-alkylamino polyol reaction products, such as N-methyl glucamine, are typically contaminated with nickel catalyst and/or contain undesirable odoriferous or colored by-products. Contamination by nickel catalyst or by-products may be tolerable if the user can afford to purify the N-alkylamino polyol prior to use. However, the manufacturer of high volume, low-cost chemicals such as detersive surfactants can ill-afford raw materials which require expensive purification steps. For example, the manufacturer of surfactants which comprise polyhydroxy fatty acid amides (e.g., $C_{10}$-$C_{20}$ fatty acid amides of N-methyl glucamine or N-methyl fructamine) requires a source of N-alkylamino polyols which have desirable low color and low odor, as well as low nickel levels. Indeed, the manufacture of high quality polyhydroxy fatty acid amide surfactants relies heavily on having a source of such high quality, yet low-cost, N-alkylamino polyols.

The present invention solves the problem of nickel contamination, odor and undesirable coloration associated with the manufacture of N-alkylamine polyols. It thereby affords access to high quality polyhydroxy fatty acid amide surfactants. Moreover, the catalytic activity of the nickel catalyst used in the present process remains high over multiple reaction sequences, thereby allowing catalyst recycle with attendant, substantial cost savings.

BACKGROUND ART

U.S. Pat. No. 2,016,962, issued Oct. 8, 1935, discloses a process for preparing glucamines and related products which involves, for example, reacting glucose, monomethylamine and hydrogen in the presence of water at temperatures around 100° C. The present invention provides a substantial improvement over the art-disclosed process, especially with regard to the quality of N-methyl glucamine produced.

U.S. Pat. No. 2,703,798, issued Mar. 8, 1955, bespeaks the problems associated with forming the condensation products of N-monoalkylglucamines and fatty acids, with respect to undesirable color characteristics and detergency properties.

SUMMARY OF THE INVENTION

The present invention encompasses, in a process for preparing N-alkylamino polyols by reacting an N-alkylamine with a reducing sugar in the presence of a nickel catalyst under hydrogen pressure, the improvement which comprises:

(a) removing substantially all oxides of nickel from the nickel catalyst (conveniently, this can be done by contacting the nickel catalyst with hydrogen, typically under pressure and temperature of 50°–185° C. at 500–1,500 psig hydrogen);

(b) admixing the nickel catalyst from (a) with the N-alkylamine to provide mixture (b) under hydrogen pressure prior to admixture with the sugar;

(c) admixing the sugar with mixture (b) under hydrogen pressure;

(d) conducting the reaction of the sugar with the N-alkyl-amine/nickel catalyst mixture (b) at a temperature below about 80° C. and under hydrogen pressure (typically at least 250 psig, preferably at least 500 psig) until at least about 95% by weight of the reducible compounds are no longer present in the reaction mixture;

(e) continuing the reaction, optionally at a temperature of up to about 120° C., until at least about 99.9% by weight of the reducible compounds are no longer present in the reaction mixture; and (f) recovering the N-alkylamino polyol, preferably without purification.

A typical process herein is wherein the nickel catalyst level is in the range of from about 5% to about 50%, most typically about 10% to about 30%, by weight of the sugar reactants, for optimal throughput.

Preferably step (d) of the process is carried out at a temperature of from about 40° C. to about 70° C. Step (e) is preferably carried out at a temperature from about 80° C. to about 120° C.

The present invention thus affords a process for the preparation of compounds which include, but are not limited to, N-alkyl glucamine, N-alkyl fructamine, N-alkyl maltamine or N-alkyl glycerol amine, comprising the steps of:

(a) admixing a nickel catalyst which is substantially free of oxides of nickel with an N-alkylamine (preferably N-methylamine);

(b) under hydrogen pressure, admixing an aqueous solution of glucose, fructose, maltose or glyceraldehyde, respectively, with the mixture from step (a);

(c) allowing the mixture from step (b) to react at a temperature of from about 40° C. to about 70° C. until at least about 95% by weight of the reducible compounds are no longer present in the reaction mixture; and (d) allowing the reaction from step (c) to continue at a temperature below about 120° C. until at least about 99.9% by weight of the reducible compounds are no longer present in the reaction mixture.

Preferably the process with glucose or fructose is conducted using nickel catalyst pre-treated with hydrogen to remove oxides of nickel, and wherein said catalyst is present at the 10% to 30% level relative to sugar.

The invention also provides a process for preparing polyhydroxy fatty acid amide surfactants, comprising reacting a member selected from the group consisting of fatty acids, fatty acid anhydrides and fatty acid esters with an N-alkylamino polyol prepared according to the foregoing manner. In a preferred process, the fatty acid ester is a $C_{10}$-$C_{18}$ alkyl or alkenyl fatty acid methyl ester and the N-alkylamino polyol is selected from N-methyl glucamine, N-methyl fructamine, N-methyl maltamine and N-methyl glycerol amine.

All percentages, ratios and proportions herein are by weight, unless otherwise specified. The pressures specified herein are pounds per square inch gauge (psig).

DETAILED DESCRIPTION OF THE INVENTION

The process of this invention employs reactants, catalysts and solvents which are known in the art. However, use of these materials in the manner disclosed herein provides superior reaction products. The following is intended to assist the manufacturer in the practice of the invention.

By "substantially free of nickel" herein is meant that the N-alkylamino polyol reaction product contains no more than about 20 parts per million (ppm) nickel, and preferably less than about 5 ppm nickel ($Ni^{++}$). Nickel can be conveniently measured by conventional atomic absorption spectroscopy, using diluted samples (5/1 dilution to minimize interference).

By "reducible compounds" or "reducibles" herein is meant chemical compounds which contain reducing sugars either in their natural state or as an adduct with the amine such as N-methylglucamine. Such compounds include, but are not limited to, species such as glucose, fructose, maltose, N-methylglucosylamine, N-methylfructosylamine, N-methyl-N-glucosylglucamine. This is measured by g.c. analysis.

By "g.c. analysis" herein is meant gas-liquid chromatography ("g.l.c.") using Hewlett-Packard 5890 Series 2 on column injection using DB1 15 meter 0.25 $\mu$ film thickness ID 250 $\mu$.

By "improved color" and/or "improved color stability" herein is meant the Gardner Color of the N-alkylamino reaction product, as produced by the present process. Moreover, the Gardner Color of the fatty amide derivatives which can be subsequently made therefrom is also substantially improved.

By "Gardner Color" herein is meant the standard Gardner measurement known in the art. A Gardner Color reading near zero (solution) represents a nearly colorless ("water-white") solution. Gardner Colors below about 7 are only marginally acceptable for the N-alkylamino polyol reaction products, and it is preferred to achieve Gardner Colors below about 4, preferably 0 to about 2. Of course, use of sugars having low Gardner Colors (e.g., 0 or 1, i.e., water-white syrups) will help ensure that N-alkylamino polyols having desirably low Gardner Colors will be produced. Stated otherwise, use of low (0–2) Gardner Color sugars (preferably white solids or water-white solutions) and use of the reaction sequence disclosed herein results in low Gardner Color N-alkylamino polyols (white or slightly off-white solids).

By "improved odor" herein is meant that the odor character of the reaction product is substantially free of amine or "fish" type odor (once any excess N-alkylamine is removed) and also substantially free of typical browning sugar odors.

By "nickel catalyst" herein is meant any of the conventional Raney nickel or "supported" nickel catalysts well-known in the art. Conventional nickel under the trademark RANEY NICKEL 4200 (Grace Chemicals) is quite suitable for use herein. RANEY NICKEL 3200 (United Catalyst, Inc.) UCI, G-96B and G-49A and G-49C are also suitable. While not intending to be limited by theory, it is believed that removing oxides of nickel from the catalyst prevents or impedes dissolution of nickel ions into the reaction milieu, and thus results in the formation of reaction products having a desirable low nickel content. Moreover, it has been found that the nickel catalyst pre-treated with pressurized hydrogen can be re-used in multiple subsequent reactions, thereby yielding a substantial overall cost savings.

By "pressurized hydrogen" or "hydrogen pressure" herein is meant: for treatment of the nickel catalyst typically 500 psig–5,000 psig; for reaction step c–d typically 200 psig–5,000 psig.

By "sugars" herein is meant reducing sugars such as glucose, fructose, mannose, lactose, maltose, xylose and the like. The term "sugars" herein also includes glyceraldehyde. Such "sugars" include plant syrups such as cane syrups, corn syrups, potato starch-derived sugar syrups, hydrolyzed wood pulp-derived sugars and the like. High fructose, high glucose and high maltose syrups are economical and preferred, especially if their Gardner Color is satisfactory.

By "N-alkylamines" herein is meant compounds such as the N-methyl, N-ethyl, N-propyl, etc., $C_1$-$C_{10}$ N-alkylamines, the corresponding hydroxy-substituted amines, e.g., ethanolamine. The $C_1$-$C_3$ alkylamines are preferred, and N-methylamine is most preferred.

The preparation of the N-alkylaminol polyols by the present process can be conducted in any well-stirred pressure vessel suitable for conducting hydrogenation reactions. In a convenient mode, a pressure reactor with a separate storage reservoir is employed. The reservoir (which, itself, can be pressurized) communicates with the reactor via suitable pipes, or the like. In use, a stirred slurry of the nickel catalyst is first treated with hydrogen to remove traces of nickel oxides. This can be conveniently done in the reactor. (Alternatively, if the manufacturer has access to an oxide-free source of nickel catalyst, pretreatment with $H_2$ is unnecessary. However, for most manufacturing processes some trace of oxides will inevitably be present, so the $H_2$ treatment is preferred.) After removal of excess slurry medium (water) the N-alkyl amine is introduced into the reactor, as disclosed in Example I. Thereafter, the sugar is introduced from the storage reservoir into the reactor either under hydrogen pressure or by means of a high pressure pumping system, and the reaction is allowed to proceed. The progress of the reaction can be monitored by periodically removing samples of the reaction mixture and analyzing for reducibles using gas chromatography ("g.c."), or by heating the sample to about 100° C. for 30–60 minutes in a sealed vial to check for color stability. Typically, for a reaction of about 8 liters (ca. 2 gallons) size the initial stage (to 95% of reducibles being depleted) requires about 60 minutes, depending somewhat on catalyst level and temperature. The temperature of the reaction mixture can then be raised to complete the reaction (to 99.9% of the reducibles being depleted).

EXAMPLE I

Catalyst Treatment—Approximately 300 mls of RANEY NICKEL 4200 (Grace Chemicals) is washed with deionized water (1 liter total volume; 3 washings) and decanted. The total catalyst solids can be determined by the volume-weight equation provided by Grace Chemicals, i.e., [(total wt. catalyst +water)—(water wt. for volume)]×7/6: Nickel solids.

308.21 g. of the catalyst Ni solids basis are loaded into a 2 gallon reactor (316 stainless steel baffled autoclave with DISPERSIMAX hollow shaft multi-blade impeller from Autoclave Engineers) with 4 liters of water. The reactor is heated to 130° C. at 1400–1600 psig hydrogen for 50 minutes. The mixture is cooled to room temperature at 1500 psig hydrogen and left overnight.

The water is then removed to 10% of the reactor volume using an internal dip tube.

Reaction—The reactants are as follows. 881.82 mls. 50% aqueous monomethylamine (Air Products, Inc.; Lot 060-889-09); 2727.3 g. 55% glucose syrup (Cargill; 71% glucose; 99 dextrose equivalents; Lot 99M501).

The reactor containing the $H_2O$ and Raney nickel prepared as noted above is cooled to room temperature and ice cold monomethylamine is loaded into the reactor at ambient pressure with $H_2$ blanket. The reactor is pressurized to 1000 psig hydrogen and heated to 50° C. for several minutes. Stirring is maintained to assure absorption of $H_2$ in solution.

The glucose is maintained in a separate reservoir which is in closed communication with the reactor. The reservoir is pressurized to 4000 psig with hydrogen. The glucose (aqueous solution) is then transferred into the reactor under $H_2$ pressure over time. (This transfer can be monitored by the pressure change in the reservoir resulting from the decrease in volume of the sugar solution as it is transferred from the reservoir into the main reactor. The sugar can be transferred at various rates, but a transfer rate of ca.100 psig pressure drop per minute is convenient and requires about 20 minutes for the volume used in this run.) An exotherm occurs when the aqueous sugar solution is introduced into the reactor; the 50° C. internal temperature raises to ca. 53° C.

Once all the glucose has been transferred to the reactor the temperature is maintained at 50° C. for 30 minutes. Hydrogen uptake is monitored by a pressure gauge. Stirring is continued throughout at 800–1,100 rpm or greater.

The temperature of the reactor is increased to 60° C. for 40 minutes, then to 85° C. for 10 minutes, then to 100° C. for 10 minutes. The reactor is then cooled to room temperature and maintained under pressure overnight. The reaction product dissolved in the aqueous reaction medium is conveniently recovered by using an internal dip tube with hydrogen pressure. Particulate nickel can be removed by filtration. Preferably, an internal filter is used to avoid exposure to air, which can cause nickel dissolution. Solid N-methyl glucamine is recovered from the reaction product by evaporation of water.

The procedure of Example I is repeated using fructose as the sugar to prepare N-methyl fructamines.

The procedure of Example I is repeated using glyceraldehyde as the sugar to prepare N-methyl glycerol amine (3-methylamino1,2-propanediol).

EXAMPLE II

In this process, the N-methyl glucamine of Example I is reacted with mixed tallow fatty acid methyl esters to prepare the corresponding tallowamide of N-methyl glucamine. It will be appreciated that coconut fatty acid methyl esters can be used in place of the tallow reactant, and various N-alkyl polyols, e.g., N-methyl fructamine, can be used in place of the N-methyl glucamine.

Reactants—N-methyl glucamine (from Example I); hardened tallow methyl esters; sodium methoxide (25% in methanol); absolute methanol (solvent); mole ratio approximately 1:1 amine:ester; initial catalyst level 10 mole % (w/r glucamine), raised to 20 mole %; solvent level 50% (wt.).

In a sealed bottle, 20.36 g of the tallow methyl ester is heated to its melting point (water bath) and loaded into a 250 ml 3-neck round-bottom flask with mechanical stirring. The flask is heated to ca. 70° C. to prevent the ester from solidifying. Separately, 12.5 g of dry N-methyl glucamine is combined with 45.36 g of methanol, and the resulting slurry is added to the tallow ester with good mixing. 1.51 g of 25% sodium methoxide in methanol is added. If after about four hours the reaction mixture is not clarified, an additional 10 mole % of catalyst (to a total of 20 mole %) can be added and the reaction allowed to continue overnight (ca. 68° C.) after which time the mixture is clear. The reaction flask is then modified for distillation. The bath temperature is increased to 110° C. Distillation at atmospheric pressure is continued for 60 minutes. High vacuum distillation is then begun. The product is allowed to remain in the reaction flask at 110° C. (external temperature) for 60 minutes. The product is scraped from the flask and optionally triturated in ethyl ether over a weekend. Ether is removed on a rotary evaporator and the product is stored in an oven overnight, and ground to a powder. The reaction product can optionally be purified for analysis, as follows. Any remaining N-methyl glucamine is optionally removed from the product using silica gel. A silica gel slurry in 100% methanol is loaded into a funnel and washed several times with 100% methanol. A concentrated sample of the product (20 g in 100 ml of 100% methanol) is loaded onto the silica gel and eluted several times using vacuum and several methanol washes. The collected eluant is evaporated to dryness (rotary evaporator). Any remaining tallow ester is optionally removed by trituration in ethyl acetate overnight, followed by filtration. The filter cake is then vacuum dried overnight. The product is the purified tallowalkyl N-methyl glucamide. NOTE: Such a high level of purification is unnecessary for routine use of the tallowalkyl N-methyl glucamide in detergent compositions, since the product will typically have an acceptable Gardner Color by virtue of the quality of the N-alkyl glucamine prepared by the instant process. Accordingly, this purification step will be at the discretion of the formulator.

In another mode, the foregoing reaction sequence can be carried out in 1,2-propylene glycol or NEODOL. At the discretion of the formulator, the propylene glycol or NEODOL need not be removed from the reaction product prior to its use to formulate detergent compositions. Again, according to the desires of the formulator, the methoxide catalyst can be neutralized by citric acid to provide sodium citrate, which can remain in the polyhydroxy fatty acid amide.

What is claimed is:

1. In a process for preparing N-alkylamino polyols by reacting an N-alkylamine with a reducing sugar and pressurized hydrogen in the presence of a nickel catalyst, the improvement comprising:
   (a) treating said nickel catalyst with hydrogen to remove nickel oxides;
   (b) admixing said nickel catalyst from (a), in an amount of from 5% to about 50% by weight of said reducing sugar, with said N-alkylamine under from about 500 to about 5,000 psig hydrogen pressure to provide a mixture;
   (c) admixing said reducing sugar with the mixture from (b) under from about 200 to 5,000 psig hydrogen pressure;
   (d) conducting the reaction of said reducing sugar with the N-alkylamine/nickel catalyst mixture (b) at a temperature below about 80° C. and under from about 200 to about 5,000 psig hydrogen pressure until at least about 95% of the reducing sugars are no longer present in the reaction mixture;

(e) continuing the reaction of step (d) at a temperature of up to about 120° C. until at least about 99.9% of said reducing sugars are no longer present in the reaction mixture; and (f) recovering the N-alkylamino polyol.

2. The process of claim 1 wherein the nickel catalyst level is in the range of from about 10% to about 30% by weight of the reducing sugar reactant.

3. The process of claim 1 wherein step (d) is carried out at a temperature of from about 40° C. to about 70° C.

4. The process of claim 1 wherein step (e) is carried out at a temperature of from about 80° C. to about 120° C.

5. The process of claim 1 wherein said N-alkylamino polyol product is selected from the group consisting of N-alkyl glucamine, N-alkyl fructamine, N-alkyl maltamine, N-alkyl glycerol amine, and mixtures thereof, and wherein the steps further comprise:

(a) admixing a nickel catalyst, pretreated with hydrogen to remove nickel oxide, in an amount from 5% to about 50% by weight of the reducing sugar, with an N-alkylamine;

(b) adding an aqueous polyol solution comprising reducing sugars selected from the group consisting of glucose, fructose, maltose, glyceraldehyde, and mixtures thereof, with the mixture from step (a);

(c) allowing the mixture from step (b) to react at a temperature from about 40° C. to about 70° C. until at least about 95% of the reducing sugars are no longer present in the reaction mixture;

(d) allowing the reaction from step (c) to continue at a temperature below about 120° C. until at least about 99.9% of the reducing sugars are no longer present in the reaction mixture; and (e) recovering the N-alkylamino polyol.

6. The process of claim 5 wherein the nickel catalyst is present at the 10% to about 30% level based on the reducing sugar.

7. The process of claim 5 wherein the N-alkylamine is N-methylamine.

* * * * *